(12) United States Patent
Shinal

(10) Patent No.: US 6,211,169 B1
(45) Date of Patent: Apr. 3, 2001

(54) STABLE CALCITRIOL SOLUTION FOR PACKAGING INTO VIALS

(75) Inventor: Edward C. Shinal, Holmdel, NJ (US)

(73) Assignee: Aesgen, Inc., Princeton, NJ (US)

( * ) Notice: Subject to any disclaimer, the term of this patent is extended or adjusted under 35 U.S.C. 154(b) by 0 days.

(21) Appl. No.: 09/408,970

(22) Filed: Sep. 29, 1999

(51) Int. Cl.$^7$ .................................................. A61K 31/59
(52) U.S. Cl. ............................................................. 514/167
(58) Field of Search .............................................. 514/167

(56) References Cited

U.S. PATENT DOCUMENTS

| | | | |
|---|---|---|---|
| 4,308,264 | * 12/1981 | Conway et al. | 424/236 |
| 4,420,092 | 12/1983 | Finkelstein et al. | 220/254 |
| 5,230,429 | 7/1993 | Etheredge, III | 206/459.1 |
| 6,051,567 | * 4/2000 | Abrahamson et al. | 514/167 |

FOREIGN PATENT DOCUMENTS

96/36340   11/1996   (WO) ............................ A61K/31/59

* cited by examiner

*Primary Examiner*—Marianne M. Cintins
*Assistant Examiner*—Donna Jagoe
(74) *Attorney, Agent, or Firm*—Schwegman, Lundberg, Woessner & Kluth, P.A.

(57) ABSTRACT

The invention provides a therapeutic calcitriol solution which is suitable for packaging into pharmaceutical vials without producing discoloration of the antioxidant component of the solution.

15 Claims, No Drawings

STABLE CALCITRIOL SOLUTION FOR PACKAGING INTO VIALS

This is a non-provisional utility patent application filed by the inventor, Dr. Edward Shinal, of Holmdel, N.J., for a "Stable Calcitriol Solution for Packaging Into Vials."

FIELD OF THE INVENTION

The invention relates to liquid calcitriol formulations, particularly calcitriol formulations for intravenous administration. More specifically, the invention relates to a calcitriol solution, and a method for preparing the solution, which is suitable for packaging into vials.

BACKGROUND OF THE INVENTION

Calcitriol, also known as 9,10-Secocholesta-5,7,10(19)-tricne-1,3,25-triol, 1 α, 25-dihydroxycholecalciferol, or 1α, 25-dihydroxyvitamin $D_3$, is the biologically active form of vitamin $D_3$ which promotes intestinal calcium transport and bone calcium resorption. It is formed in the kidney during the second of two successive hydroxylations of vitamin D, and is administered therapeutically for the treatment of vitamin D-dependent rickets, osteoporosis, hypocalcemia (particularly when associated with hypoparathyroidism), and calcium metabolism disorders associated with renal failure.

Calcitriol is supplied commercially in two forms. Rocaltrol® (calcitriol) capsules (Roche Labs) provide a solid form for oral administration, while Calcijex® (calcitriol) (Abbott Labs) provides a solution for intravenous administration, which is particularly useful for chronic renal dialysis patients. The intravenous solution is supplied as 1 ml ampules containing either 1 mcg or 2 mcg of calcitriol. The ampules are stored at 15–30° C. (59–86° F.) and are formed of amber glass to protect the solution from light.

Calcitriol is a colorless compound which can be degraded by light and oxygen. Therefore, it is supplied in combination with a metal ascorbate salt antioxidant, such as sodium ascorbate, and a chelating agent. The headspace of the calcitriol ampule is filled with nitrogen gas to provide an inert atmosphere. However, even in the airtight ampule, the solution retains some oxygen and the reaction of the metal ascorbate antioxidant with the residual oxygen ultimately causes the clear solution to turn yellow. Since drug products are periodically inspected for discoloration, a significant amount of therapeutically useful product is discarded due to antioxidant discoloration.

A calcitriol composition which is stored in an ampule has previously been described by Conway et al. (U.S. Pat. No. 4,308,264, issued Dec. 29, 1981). Although the sealed glass ampule provides the advantage of product storage with nitrogen gas in the headspace to provide a more inert environment, this form of drug packaging has even more significant disadvantages for clinical use. For example, sealed glass ampules must be broken open in order to access the medication, exposing the health care provider to risk of injury from broken glass. Glass fragments can enter the solution as the ampule is broken, often requiring the use of a sterile filter, with additional effort and expense, to remove the solution from the open ampule. Breaking the ampule requires that it be handled, usually not within a sterile environmnent, increasing the risk of both microbial and blood contamination. The ampule has broken glass edges which are difficult to sterilize before the needle is inserted. Once the ampule is broken the entire contents must be used or, if only a part of the contents are used, the remainder must be discarded. It is also not unusual for an ampule to shatter completely upon opening, spilling the contents and potentially causing injury to the individual trying to open it. Ampule packaging is therefore used only when the physical and chemical stability of the contents requires it.

There is currently a need for alternative packaging systems that can maintain the stability of aqueous calcitriol solutions.

SUMMARY OF THE INVENTION

The invention provides a therapeutic aqueous calcitriol solution which has a molecular oxygen concentration of less than about 1 ppm, and more preferably less than about 0.5 ppm or less, the solution being resistant to antioxidant discoloration. The invention also provides said solutions packaged into containers such as ampules or pharmaceutical vials. Suitable vials are those comprising a closure means comprising a septum (i.e., a closure means that is penetrable and self-sealing).

The invention also provides a method for limiting discoloration of a therapeutic calcitriol solution by preparing the solution with water which has been purged of oxygen, to yield an oxygen concentration of less than 1 ppm, and more preferably less than about 0.5 ppm.

Further, the invention also provides a novel dosage form for calcitriol comprising an aqueous calcitriol solution packaged in a pharmaceutical vial, such as the pharmaceutical vials described by Etheredge (U.S. Pat. No. 5,230,429, issued Jul. 27, 1993, and incorporated herein by reference), the stopper preferably being at least partially coated with an inert polymer, such as polytetrafluoroethylene (Teflon® (polytetrafluoroethylene), DuPont®, Wilmington, Del.), so as to prevent chemical interaction between any of the other stopper components and the calcitriol solution.

DETAILED DESCRIPTION

The inventor has discovered a method to stabilize the antioxidants responsible for the discoloration of a therapeutic calcitriol solution, thereby providing a solution which can be packaged into vials. Until now, it has not been practical to package calcitriol in vials, since the available molecular oxygen in the solution causes the antioxidant, which protects the drug from chemical degradation, to be degraded to form colored (usually yellow) compounds. Although the calcitriol solution is chemically stable in the presence of the antioxidant, it is perceived as being degraded when the solution turns yellow.

Applicant has discovered that calcitriol solutions prepared from water having a dissolved oxygen level of less than 1 part per million, and preferably less than about 0.5 parts per million, undergo significantly less antioxidant degradation than conventional aqueous calcitriol solutions.

The therapeutic calcitriol solution of the present invention can be packaged into ampules or into glass vials, most preferably vials of amber glass to protect the calcitriol from degradation by light. The concentration of calcitriol in the therapeutic solution is preferably from approximately 0.5 mcg/ml to approximately 3 mcg/ml, and most preferably about 1.0 mcg/ml to 2.0 mcg/ml.

Glass vials that can be used for packaging the solution of the present invention are commonly used for packaging injectable solutions and are known to those of skill in the art. Examples of glass vials which can be used to package calcitriol intravenous solution dosage forms are described, for example, in U.S. Pat. No. 5,230,429 (Etheredge, Jul. 27, 1993). The vial typically has a closure means, usually a stopper, formed of rubber or other polymeric material, which allows a needle to be inserted therethrough into the vial without requiring that any glass be broken. A preferred stopper has an inert (e.g., polytetrafluoroethylene (Teflon®, DuPont®, Wilmington, Del.)) coating to prevent chemical interaction between the stopper components and the calcitriol solution. The closure or stopper is typically held securely in place by a metal over-cap, which in turn has an exterior cover used to seal the vial until its initial use. The polymer closure means comprises at least one septum, or thinner area of polymer material, preferably centered in the body of the closure means, through which a needle can be inserted to contact the solution. The solution can be drawn into the needle without glass particle hazard to either the patient or the health care provider.

Although Conway et al. (U.S. Pat. No. 4,308,264) describe a process of boiling the water used to prepare an aqueous calcitriol solution, this method does not reduce the oxygen level sufficiently to provide a solution that can be packaged in vials with an antioxidant, without unacceptable degradation (yellowing) of the antioxidant.

Since water has a mole fraction solubility ($X_1$) at 25° C. of $2.29 \times 10^{-5}$ (R. Battino, Ed. *IUPAC Solubility Series, Vol. 7: Oxygen and Ozone* (1981), Pergamon Press, Oxford England), the inherent solubility of oxygen is therefore 409 parts per million (ppm). When efforts, such as boiling the water or sparging with nitrogen, are made to exclude oxygen, it is possible to reduce the oxygen concentration to 3 to 6 ppm. However, even 2 ppm oxygen concentration is sufficient to induce antioxidant degradation and solution discoloration. Water in a batching vessel will equilibrate above one percent, even if constant sparging of nitrogen (as is commonly practiced in the pharmaceutical industry) is performed.

The present invention provides a calcitriol solution which resists discoloration when an antioxidant is present in the solution, and a method for preparing such a calcitriol solution, by lowering and maintaining the oxygen content of the solution to about 0.5 ppm or less prior to packaging. Briefly, the calcitriol solution vial is prepared using Water for Injection, USP, which has been purged of essentially all oxygen, to a level of less than 0.5 parts per million, preferably in a closed top vessel. The closed top vessel is important to the invention, since an open top vessel allows trace oxygen from the atmosphere to redissolve in the water. The calcitriol solution is placed into a suitable vessel, where nitrogen is directed to flow through sintered dispersion heads located at or near the bottom of the liquid volume, with the only exit port being a vent for excess nitrogen. An inert atmosphere is also maintained above the solution throughout the process of mixing the solution, filling the solution into vials, and closure and sealing of vials to yield a final product with a dissolved oxygen content of less than 0.5 ppm and a headspace oxygen content of less than 0.5 ppm. Nitrogen, for example, can be used to provide the inert atmosphere.

Generally, a calcitriol solution prepared by the method of the present invention will comprise, for example, about 1 mcg to about 2 mcg calcitriol, in admixture with about 1,000 to 15,000 parts, or, for example, about 10 mg/ml, ascorbate antioxidant, about 8 to about 12,000 parts, or approximately 1 mg/ml, of a chelating agent, with approximately 400 to approximately 80,000, or approximately 4 mg, of a surfactant, and added water sufficient to produce the desired solution volume. Preferably, the added water is Water for Injection, USP, which has been sparged with nitrogen in a closed top vessel to produce an oxygen concentration of less than about 1, and preferably less than about 0.5, parts per million. The solution is maintained at a pH of approximately 6.5 to 7.8 using dibasic and monobasic sodium phosphate.

The solution is sparged with nitrogen or other noble gas, as described above, and as the vials are filled and sealed a suitable atmosphere is maintained (using nitrogen or other noble gas, for example) to keep the oxygen concentration level at or below 1 ppm, or more preferably below 0.5 ppm.

A solution such as that described above, prepared by the method of the present invention, can be stored at 15 to 30° C. for a period of at least two years without exhibiting solution discoloration, discoloration being determined using APHA color standards by methods known to those of skill in the art.

The invention will be further described by the following example.

EXAMPLE

A color-stabilized, chemically stable, sterile, dilute aqueous calcitriol (1 α, 25-dihydroxycholecalciferol) solution packaged in amber glass vials having a rubber/teflon closure and metal over-cap was prepared by placing 3300 ml of Water for Injection, USP, at a temperature of 15–30° C., into a 45.5 liter Kimax ®solution bottle (No. 16144-087, VWR Scientific, Buffalo Grove, Ill.) having a vented cover. Nitrogen, NF, was sparged through the water using sintered diffuision devices to produce fine nitrogen bubbles through the bulk liquid. Sparging was continued until a dissolved oxygen concentration of 0.09 ppm was reached. Sodium chloride (45.6 grams) and edetate disodium, dihydrate (33.43 grams) were added, and mixed under a nitrogen blanket until dissolved (less than 5 minutes). Sodium phosphate, monobasic (54.7 grams) and sodium phosphate, dibasic (231 grams) were added and mixed under a nitrogen blanket until dissolved. Sodium ascorbate (303.9 grams) was added, and mixing continued for more than 2 minutes to provide a bulk solution.

In a nitrogen atmosphere glove bag, 0.07583 gram of calcitriol was added to 121.6 grams of polysorbate 20 (a non-ionic surfactant), and mixed. This solution was mixed with the bulk solution under nitrogen.

Vials were filled under nitrogen atmosphere, using parallel in-line nitrogen flushing. Each 2 ml amber glass vial received 1.25 ml of solution, and a stopper was loosely placed over the vial opening. Trays of filled and stoppered vials were placed in a lyophilizer to provide complete exchange of headspace atmosphere with nitrogen, and the stoppers were internally seated before the vials were exposed to the general atmosphere. An alternate method for sealing would place the vials within a zero oxygen tunnel such as that commercially available from Modified Atmosphere Packaging Systems (Des Plains, Ill.).

The invention is described with reference to various specific and preferred embodiments and techniques. However, it should be understood that many variations and modifications may be made while remaining within its scope.

All referenced publications, patents and patent documents are incorporated by reference, as though individually incorporated by reference.

What is claimed is:

1. An aqueous solution comprising calcitriol, an antioxidant, a chelating agent, and less than about 1 ppm molecular oxygen.

2. The solution of claim 1 comprising less than about 0.5 ppm molecular oxygen.

3. The solution of claim 1 wherein the calcitriol concentration is about 1 mcg/ml to about 2 mcg/ml.

4. A dosage form comprising the aqueous calcitriol solution of claim 1, 2 or 3 packaged in a vial.

5. The dosage form of claim 4 wherein the vial comprises a closure means comprising a stopper that comprises a coating of polytetrafluoroethylene that prevents chemical interaction between said solution and other components of the stopper.

6. A method for preparing an aqueous calcitriol solution comprising an antioxidant and a chelating agent which can be stored in a vial without significant antioxidant discoloration, comprising: (a) preparing a solution of calcitriol, antioxidant and chelating agent with water which solution has been purged of molecular oxygen under an inert atmosphere to yield a final concentration of less than about 1 ppm oxygen; and (b) packaging said solution in a vial under an atmosphere suitable to maintain the oxygen content of the solution at less than about 1 ppm.

7. The method of claim 6 further comprising packaging the solution under an atmosphere suitable to maintain the oxygen concentration below about 0.5 ppm.

8. The method of claim 6 wherein the water is sparged with nitrogen in a closed chamber.

9. The method of claim 6 wherein the antioxidant is ascorbate.

10. The solution of claim 1 wherein the chelating agent is edetate disodium, dihydrate.

11. The solution of claim 1 wherein the antioxidant is an ascorbate antioxidant.

12. The solution of claim 1 wherein the solution is maintained at a pH of about 6.5–7.8 using dibasic and monobasic sodium phosphate.

13. The method of claim 6 wherein the chelating agent is edetate disodium, dihydrate.

14. The method of claim 6 wherein the solution is maintained at a pH of about 6.5–7.8 using dibasic and monobasic sodium phosphate.

15. The method of claim 6 wherein the vial comprises a stopper comprising a coating of polytetrafluoroethylene that prevents chemical interaction between the solution and other components of the stopper.

* * * * *